(12) United States Patent
Loffler et al.

(10) Patent No.: US 6,572,633 B1
(45) Date of Patent: Jun. 3, 2003

(54) CATHETER

(75) Inventors: Edgar German Loffler, Kleve (DE); Arie Luite Visscher, Driebergen (NL)

(73) Assignee: Delft Instruments Intellectual Property B.V., Delft (NL)

( * ) Notice: Subject to any disclaimer, the term of this patent is extended or adjusted under 35 U.S.C. 154(b) by 0 days.

(21) Appl. No.: 09/051,414

(22) PCT Filed: Jul. 4, 1997

(86) PCT No.: PCT/NL97/00384
§ 371 (c)(1),
(2), (4) Date: Mar. 3, 1999

(87) PCT Pub. No.: WO98/01183
PCT Pub. Date: Jan. 15, 1998

(30) Foreign Application Priority Data

Jul. 5, 1996 (NL) .............................................. 1003527

(51) Int. Cl.[7] .............................................. A61M 29/00
(52) U.S. Cl. .................................. 606/192; 604/101.03
(58) Field of Search ................................ 606/192, 194, 606/196, 191; 604/101.01, 101.02, 101.03

(56) References Cited

U.S. PATENT DOCUMENTS

| 4,781,681 A | | 11/1988 | Sharrow et al. |
|---|---|---|---|
| 4,921,478 A | | 5/1990 | Solano et al. |
| 5,279,546 A | * | 1/1994 | Mische et al. ......... 604/101.03 |
| 5,306,250 A | | 4/1994 | March et al. |
| 5,540,659 A | | 7/1996 | Teirstein |
| 5,556,389 A | | 9/1996 | Liprie |
| 5,618,266 A | | 4/1997 | Liprie |
| 5,643,171 A | | 7/1997 | Bradshaw et al. |
| 6,068,611 A | * | 5/2000 | Loffler et al. ................ 606/192 |
| 6,196,996 B1 | * | 3/2001 | Teirstein ................ 604/101.01 |

FOREIGN PATENT DOCUMENTS

DE            91 02 312        6/1992

* cited by examiner

Primary Examiner—Kevin T. Truong
(74) Attorney, Agent, or Firm—Birch, Stewart, Kolasch & Birch, LLP

(57) ABSTRACT

A catheter provided with an elongated tube having channels for the guiding of a radioactive element and for the passage of a guide wire for the catheter as well as fluid under pressure, in which the elongated tube is provided near its distal end on its outer circumference with a recanalization balloon and activatable centering means arranged therein. A by-pass can also be arranged through the recanalization balloon.

9 Claims, 2 Drawing Sheets

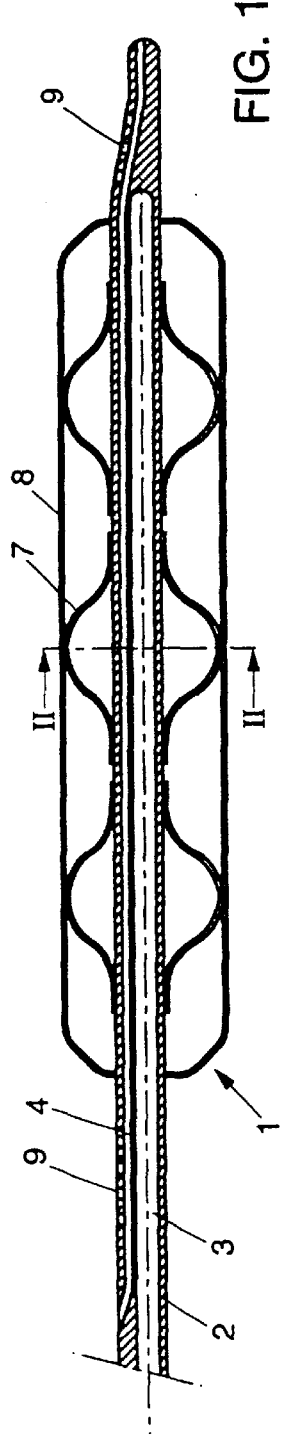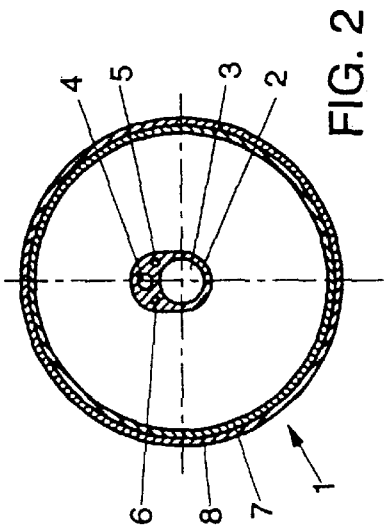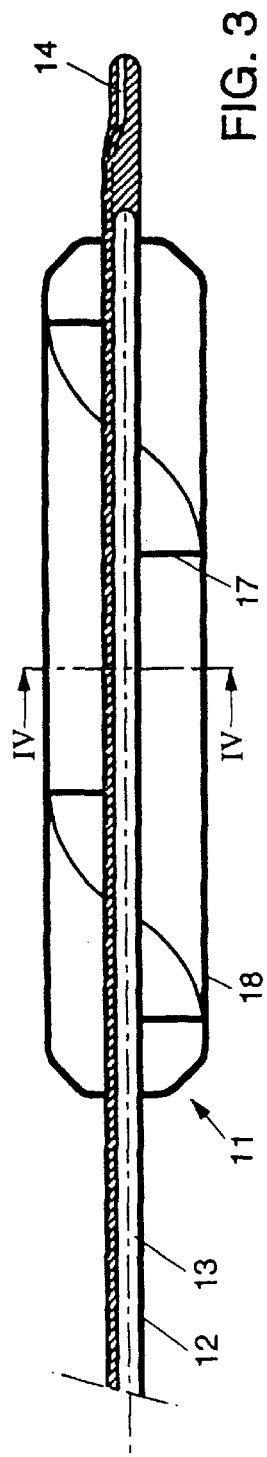

CATHETER

BACKGROUND OF THE INVENTION

1. Field of the Invention

The present invention relates to a catheter comprising an elongated tube having a first channel for the guiding of a radioactive element and a second channel for the passage of a guide wire for the catheter, the elongated tube being provided with temporarily activatable centering means on its outer circumference near its distal end.

2. Description of the Related Art

Such a catheter known from EP-A-0 688 580 is intended for use after a recanalization treatment in which a substantially occluded blood vessel (for example as a result of the deposition of so-called plaque within the lumen of the blood vessel) is stretched by means of an expandable element such as a fluid-inflatable recanalization balloon, fastened at the distal end of an elongated catheter tube in order to permit the blood to flow unimpeded through the stretched blood vessel.

If is frequently found after a relatively short period of time that a new recanalization treatment is necessary because a constriction is again forming in the blood vessel or has already formed. The constriction may be a consequence of tissue developing at the stretched place (known as neointima proliferation), probably due to the fact that the wall of the blood vessel is damaged by the stretching. This formation of tissue can be prevented to a large extent, or at least reduced, if, during or shortly after the recanalization treatment, the blood-vessel tissue in question is irradiated with ionizing radiation, in particular β and/or γ radiation.

For such a treatment, the catheter known from EP-A-0 668 580 can be used. The intensity of radiation of the radioactive element introduced decreases greatly with the distance. In order not to permit the radiation dose to be too great (damaging of vessel wall) or too low (not the intended reduction of tissue developing at the stretched place), it is important to center the radioactive element accurately in the blood vessel. This is done in the known catheter by centering means in the form of an inflatable balloon which is subdivided by constriction means into a plurality of balloon parts. The constriction means are so dimensioned that the different balloon parts communicate with each other.

Upon such a treatment, therefore, the recanalization catheter must first of all be brought to the desired place and after the carrying out of the recanalization treatment, be removed and replaced by the catheter for the guiding of the radioactive element, in which connection, of course, great care must be paid to the fact that the radioactive element can be placed precisely at the place of the earlier recanalization treatment. All in all a cumbersome and timeconsuming method which must be carried out extremely cautiously, while, also from the standpoint of the patient who must undergo the treatment, it is preferable for it to be carried out as rapidly and efficiently as possible.

SUMMARY OF THE INVENTION

The object of the present invention thus is also the provision of such an instrument that the treatment can be carried out in a short time effectively and reliably with as few manipulations as possible.

This is achieved, in accordance with the present invention, by a catheter of the type described above in the manner that the centering means are surrounded by a recanalization balloon which is inflatable by a fluid introduced via a third channel so as to form an elongated body and in the manner that the centering means are activatable within the recanalization balloon. By these measures, the recanalization treatment and the irradiation treatment of the stretched region of the blood vessel can be carried out with one and the same catheter, in other words rapidly and without loss or time, since a catheter removal action and introduction action are avoided, which also is particularly valued by the patient. Furthermore, the fact that it is not necessary to change the catheter has the particular additional advantage that the centering means are automatically located at the precisely desired place so that, in addition, there is also obtained a guarantee that the radiation will always be carried out at the correct place as well as in the correct manner.

The activating of the centering means can in this connection be carried out both simultaneously with and by the inflating of the recanalization balloon as well as independently thereof, in particular after the carrying out of the recanalization treatment.

The activating of the centering means simultaneously with the inflation of the recanalization balloon can take place automatically if, in accordance with another embodiment of the invention, the centering means are connected, on the one hand, to the recanalization balloon and, on the other hand, to the tube, all in such a manner that the tube is centered in the recanalization balloon upon the inflation thereof. The centering means can, in this connection, consist, for instance, of a number of annular parts of thin plastic material which, for the introduction of the catheter, can be laid compactly around the tube together with the recanalization balloon around the tube, and by the inflation of the recanalization balloon, come into a position extending transversely on the tube in order thus to center the tube with respect to the recanalization balloon. Furthermore, the centering means can have wire-shaped parts which, in the inflated condition of the recanalization balloon, extend radially with respect to the tube.

In accordance with another embodiment of the invention, it is also preferable for the centering means to comprise inflatable balloon means which are inflatable by fluid introduced via the third channel, the balloon means comprising a plurality of balloons which center the part of the first channel protruding between the balloons with respect to the recanalization balloon.

If preference is given to the centering means being activatable independently of the recanalization balloon, for instance after the recanalization treatment has been completed, then, in accordance with a further embodiment of the invention, it is preferred that the centering means comprise inflatable balloon means which are inflatable by fluid introduced via at least a fourth channel arranged in the tube, in which connection the balloon means comprise a number of balloons which center the part of the first channel extending between the balloons with respect to the outer circumference of the recanalization balloon. The centering balloons may consist of a plurality of balloons arranged one behind the other along the tube or of a plurality of elongated balloons which lie radially alongside of each other around the tube.

The use of the same catheter for both the recanalization treatment and the irradiation treatment results in a longer continuous dwell time of the catheter at the place of treatment than in the case of two successively introduced catheters. In this connection, it is preferred in accordance with a further embodiment of the invention that a further channel be present which extends from a distal place past the recanalization balloon and the centering means to past the proximal end of the recanalization balloon and the centering means and is provided on opposite sides of the recanalization balloon and the centering means with at least one communicating opening with the surroundings. By these measures, the flow of the blood through the treated blood vessel can remain undisturbed to a far-reaching extent, which makes special measures with regard to this generally unnecessary. This effect can be realized in particularly advantageous manner if, in accordance with another preferred embodiment of the invention, the further channel coincides with the second channel, in which case the guide wire can be pulled further back from the distal end of a second channel than the proximal connecting opening or openings. Therefore, use is made in advantageous manner of the existing channel for the guide wire, as is directly possible since the guide wire, after bringing the catheter to its place, has no further active function to perform and can be withdrawn without problems into a waiting state.

BRIEF DESCRIPTION OF THE DRAWINGS

Referring to the embodiment shown diagrammatically in the drawing, the catheter of the invention will now be explained in further detail. In the drawing:

FIG. 1 shows a first embodiment of the catheter of the invention, in longitudinal section;

FIG. 2 shows, on a larger scale, a cross section along the line II—II of FIG. 1;

FIG. 3 shows a second embodiment of the catheter of the invention, in longitudinal section;

DETAILED DESCRIPTION OF THE INVENTION

Figure 5:
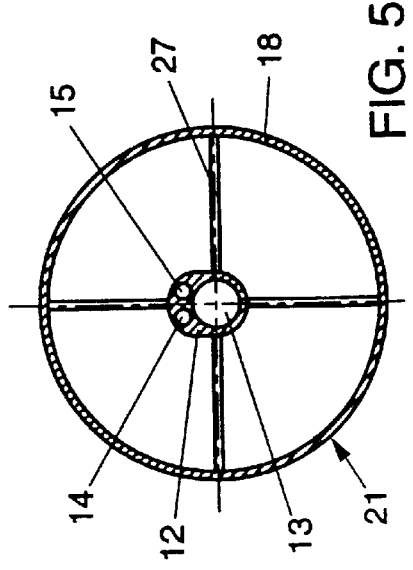
FIG. 5 shows, in the manner of FIGS. 2 and 4, a third embodiment of the catheter in accordance with the invention.

FIGS. 1 and 2 show a catheter 1 which is provided with a tube 2 having a first channel 3, a second channel 4, a third channel 5, and a fourth channel 6. On the tube 2 there are provided inflatable centering balloons 7 which are arranged fast and sealed-off one behind the other, they being surrounded by a recanalization balloon 8 which is also inflatable and the ends of which are also fastened firmly and sealed-off on the tube 2.

The first channel 3 is intended for the conducting of a radioactive element (not further shown) having a generally elongated shape, the length of the radioactive element being adapted to the length of the part of the blood vessel to be irradiated which has been previously subjected to the recanalization treatment, and the cross section of the radioactive element is adapted to the cross section of the first channel 3, all in such a manner that the radioactive element can be brought guided displaceably through the first channel 3 to and from the irradiation position. For this purpose, the radioactive element can be fastened to the end of a transport wire which is also to be displaced through the first channel 3. The first channel 3 has a closed distal end which can serve as stop surface for the precise positioning of the radioactive element.

The second channel 4 is intended for the receiving and passage of another guide wire, not shown but generally known, which, upon the introduction of the catheter 1, is first pushed in and through the blood vessel and over which the catheter is pushed. In this connection, it is pointed out that various techniques are known for introducing a balloon catheter into a blood vessel. As first technique, mention may be made of the so-called fixed-wire system, also known as the "on-the-wire system". A second technique is the socalled "over-the-wire" technique, in which the balloon catheter can be shoved over the guide wire and displaced. In accordance with a third technique, use is made of a balloon catheter, a relatively short segment of which is provided with a channel having an inlet and an outlet, the guide wire extending through this channel so that the catheter can be pushed along the guide wire. This last technique is generally referred to as the monorail system. This monorail system is also preferably, but not strictly necessarily, used in catheters in accordance with the present invention. In the embodiment shown in FIG. 1, the channel 4 makes the catheter suitable for use of the monorail technique. The second channel 4, in front of and behind the places where the recanalization balloon 8 is connected to the tube 2 is provided with openings 9 which connect the second channel 4 with the surroundings, that is to say, when the catheter is introduced, with the inside of the blood vessel treated. Furthermore, the second channel 4 does not extend over the entire length of the tube 2, but from the distal end of the tube 2 where the second channel 4 terminates in an open mouth 10, up to and some distance past the openings 9 located furthest from the open mouth 10.

The third channel 5 (FIG. 2) is intended for the feeding of fluid by gas and/or liquid to the recanalization balloon 8. For this purpose, openings are present in the wall of the tube 2 in the third channel 5 within the recanalization balloon 8 but outside the central balloons 7.

The fourth channel 6 (FIG. 2) is intended for the feeding of fluid (that is to say gas and/or liquid) to the centering balloons 7. For this purpose, openings are present in the wall of the tube 2 within each centering balloon.

For the performing of a recanalization and irradiation treatment, the guide wire, travelling through the second channel 4 with its distal end extending past the open mouth 10 is inserted into the blood vessel and guided therein in the customary, known manner in the direction of the blood vessel wall to be treated. The catheter 1 is inserted, with balloons 7 and 8 uninflated, through the same opening as the guide wire in the blood vessel and follows the guide wire upon the further displacement. After the distal end of the catheter has thus been brought to the desired place, the guide wire can, if desired, be withdrawn to past the openings 9 located furthest from the open mouth 10, as a result of which the circulation of blood through the blood vessel can take place undisturbed to a far-reaching extent. Furthermore, via the third channel 5, fluid is fed for the inflating of the recanalization balloon 8 for the carrying out of the first phase of the treatment—the stretching of the blood vessel. After this has been done, the fluid fed is discharged again via channel 5 and fluid is fed via the fourth channel 6 for the inflating of the centering balloons 7 whereby, as can be noted from FIG. 2, the tube 2 is so positioned in the blood vessel that the center line of the first channel 3 is centered in the centering balloons and thus also positioned in the blood vessel. The catheter 1 is then in an optimal condition of irradiation. The irradiation is effected by displacing the radioactive element through the first channel 3 until it comes against the end of the first channel 3 and, after being held in place for the desired period of time, is pulled back again and removed from the body of said radioactive element. Finally, after allowing the balloons to empty, the catheter is removed and the treatment is completed.

Figure 4:
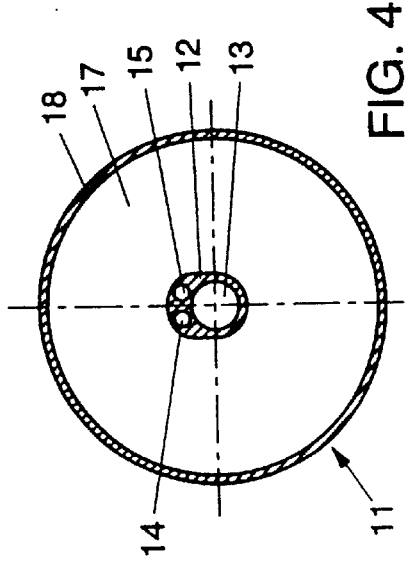
FIG. 4 shows, on a larger scale, a cross section along the line IV—IV of FIG. 3.

In FIGS. 3 and 4, a catheter 11 is shown which is provided with a tube 12 having a first channel 13, a second channel 14, and a third channel 15. Around the tube 12, at the distal end thereof, there is arranged a recanalization balloon 18 which, as customary, has an elongated shape and is connected at its ends firmly and in sealed fashion to the tube 12. Between the tube 12 and the recanalization balloon 18 there extends a centering means in the form of a strip 17 of a thin flexible material extending helically around the tube 12. The width of the strip 17 agrees with the distance between the tube 12 and the recanalization balloon 18 in inflated state. The strip 17 is fastened to both the tube 12 and to the recanalization balloon 18.

The first channel 13 is intended for the guiding of a radioactive element (any further) of the same type as already described above. Like the first channel 3 in FIG. 1, the first channel 13 has a closed distal end which can serve as stop surface for the accurate positioning of the radioactive element. The second channel 14 is intended for the receiving and passage of a guide wire, not shown any further but generally known. The second channel 14 is provided, in front of and behind the places where the recanalization balloon 8 is connected to the tube 2, with openings which connect the second channel 4 with the surroundings, that is to say, when the catheter is present, with the inside of the blood vessel treated. Said openings are present in FIG. 3 behind the plane of the drawing and have the same function as the openings 9 in the catheter 1 of FIGS. 1 and 2. The third channel 13 (FIG. 4) is intended for the feeding of fluid to the recanalization balloon 18. For this purpose, openings (not shown) are provided in the wall of the tube 12 in the third channel 15 within the recanalization balloon 8. In view of the fact that the strip 17 extends helically around the tube 12, in principle one opening should be sufficient. Of course, it is also possible to apply more than one strip 17, in which case each screw thread thus formed must be able to be fed with fluid in order to be able to carry out the recanalization treatment in the manner desired, which can be effected in a manner similar to that described above in connection with the catheter of FIGS. 1 and 2. In this connection, the centering function of the centering balloons 7 in the case of the catheter 1 will be taken over in the case of catheter 11 by the strip 17 which, upon the inflation of the recanalization balloon 18, assume the helical position extending perpendicular to the tube 12 and the wall of the recanalization balloon 18 and in this way, as shown in FIG. 4, centers the axis of the first channel 13 with respect to the recanalization balloon 18 and therefore the wall of the blood vessel to be treated.

It is pointed out that in the event that two strips 17 are arranged within the recanalization balloon 18, as well as use is made of a tube 2 such as shown in FIGS. 1 and 2 in which the one screw thread within the recanalization balloon 18 is fed by the third channel 5 and the other screw thread by the fourth channel 6 in the tube 2, it is possible, after the recanalization treatment, to relieve one of the screw threads of the fluid pressure or even bring it under a slight vacuum, as a result of which a helical passage is created around the outside of the recanalization balloon for the circulation of the blood through the blood vessel. If desired, one or the other screw thread can alternately perform the passage function.

FIG. 5 shows in cross section a catheter 21 which is substantially identical to that of FIGS. 3 and 4, as can be noted from the identical reference numerals. The difference is that in this embodiment the strip 17 is replaced by thread-shaped elements 27 which are connected on one side to the tube 12 and on the other side to the recanalization balloon 18. Upon the inflation of the recanalization balloon 18, the thread-shaped elements 27 will center the axis of the first channel 13 with respect to the recanalization balloon 18 and in this way the blood vessel wall to be treated.

Figure 6:
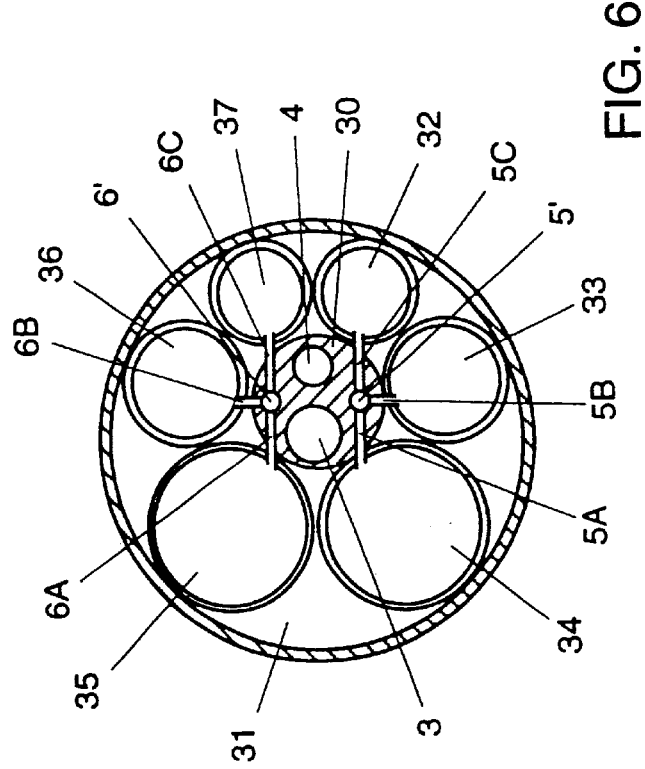
FIG. 6 shows, in a cross section, a fourth embodiment of a catheter in accordance with the invention.

FIG. 6 shows, diagrammatically in cross section, an embodiment of a catheter in accordance with the invention in which the centering means, in the same way as in the embodiment of FIG. 1, comprise a plurality of balloons. The centering balloons of the embodiment shown in FIG. 6 are, however, not arranged one behind the other in the longitudinal direction of the catheter as in FIG. 1, but are radially distributed around the central tube 30. FIG. 6 shows six centering balloons 32 to and including 37 which are arranged within a recanalization balloon 31 around the central tube 30. The centering balloons have an elongated shape with a length which is as great as that covered by the recanalization balloon or at least a considerable part thereof. In the example shown, the elongated centering balloons can be inflated via the channels 5 and 6, which are provided for this purpose with transverse holes 5a, 5b, 5c and 6a, 6b, 6c respectively. The elongated balloons lie radially around the tube 2. Since, however, the channel 3 which serves for the guiding of the radioactive element is not centered in the tube, the diameter of the elongated balloons is varied in accordance with whether they are closer to or further from the channel 3, so that the centering balloons in inflated state accurately center the channel 3 with respect to the recanalization balloon 31 which lies against the wall of the blood vessel. It is pointed that each elongated balloon may be a combination of a number of balloons located one behind the other.

It is obvious that, within the scope of the invention as set forth in the accompanying claims, a large number of modifications and variants are furthermore possible. Thus the first channel can also be used for the feeding of fluid to the balloons, so that the third and/or fourth channels could be dispensed with. In this connection, it could be that the first channel is not used during the recanalization treatment so that it is available for the feeding of fluid under pressure to the recanalization balloon. If no pressure is desired in the first channel during the transporting of the radioactive element, then a separate channel may be present in the embodiment with the centering balloons or the double screw thread for the operating of the centering means. Furthermore, the first channel could be used for the guide wire, since guide wire and radioactive element are not used at the same time. This possibility, however, is less preferable since the first channel must then be open at its distal end and the radioactive element may come into contact with blood.

Furthermore, depending on the intended use of the catheter, the second channel 4 or 14 can be located exclusively in the front end of the catheter, that is to say between the balloon means and the distal end. These and similar modifications are obvious to those skilled in the art.

What is claimed is:

1. A catheter for recanalization and irradiation of an occluded blood vessel, comprising:
   an elongated tube having proximal and distal ends;
   a first channel in the tube and being adapted to receive and guide a radioactive element near the distal end, said first channel having a closed distal end;
   a second channel in the tube adapted to receive and pass therethrough a guide wire;

temporarily activatable centering means on an outer periphery of the tube near the distal end thereof, such that when the centering means are activated the radioactive element is centered in the occluded blood vessel; and temporarily activatable recanalization means surrounding the centering means to recanalize the occluded blood vessel;

wherein upon activation of the recanalization means, no passage of blood through the blood vessel is possible, and the catheter comprises means for allowing the passage of blood through the blood vessel during irradiation once the centering means are activated.

2. The catheter according to claim 1, further comprising at least one further channel which extends from a distal place past the recanalization means and the centering means to past the proximal end of the recanalization means and the centering means and is provided on opposite sides of the recanalization means and the centering means with at least one connecting opening with the surroundings.

3. The catheter according to claim 2, wherein said further channel coincides with the second channel, in which connection the guide wire can be pulled back further from the distal end of the second channel therein than the proximal connecting opening.

4. The catheter according to claim 1, wherein the recanalization means comprises at least one fluid inflatable recanalization balloon surrounding the centering means;

wherein the tube comprises a third channel for feeding an inflating fluid into recanalization balloon; and wherein the centering means are activatable within the recanalization balloon.

5. The catheter according to claim 4, wherein the centering means comprises at least one fluid inflatable balloon located on an outer periphery of the tube near the distal end and wherein the tube comprises a fourth channel for feeding an inflating fluid into the recanalization balloon.

6. The catheter according to claim 5, wherein the centering means comprises at least one strip-shaped member of a thin flexible member fastened to both the tube and the recanalization balloon.

7. The catheter according to claim 6, wherein the width of the strip-shaped member agrees with the distance between the tube and the recanalization balloon in inflated state.

8. The catheter according to claim 6, wherein the strip-shaped member extends helically around the tube.

9. The catheter according to claim 6, wherein the strip-shaped member extends perpendicular to the tube and the recanalization balloon.

* * * * *